(12) United States Patent
Harada (10) Patent No.: US 7,090,805 B2
(45) Date of Patent: Aug. 15, 2006

(54) TASTE RECOGNITION SYSTEM AND RECOGNITION METHOD

(75) Inventor: Tsutomu Harada, Aichi (JP)

(73) Assignee: Eisai Co., Ltd., Tokyo (JP)

( * ) Notice: Subject to any disclaimer, the term of this patent is extended or adjusted under 35 U.S.C. 154(b) by 289 days.

(21) Appl. No.: 10/191,495

(22) Filed: Jul. 10, 2002

(65) Prior Publication Data

US 2003/0013198 A1    Jan. 16, 2003

(30) Foreign Application Priority Data

Jul. 11, 2001 (JP) .............................. 2001-210311

(51) Int. Cl.
| | |
|---|---|
| G01N 15/06 | (2006.01) |
| G01N 33/00 | (2006.01) |
| G01N 33/48 | (2006.01) |
| G01N 35/00 | (2006.01) |
| C12Q 1/68 | (2006.01) |

(52) U.S. Cl. .................... 422/68.1; 422/50; 422/69; 422/81; 422/82; 422/82.01; 422/82.02; 422/82.03; 422/99; 422/100; 422/101; 422/102; 422/103; 422/104; 436/43; 436/52; 436/53; 436/63; 436/174; 436/178; 436/180; 73/1.01; 73/1.02; 73/53.01

(58) Field of Classification Search ............ 422/50, 422/68.1, 69, 81, 82, 82.01, 82.02, 82.03, 422/99, 100, 101, 102, 103, 104; 436/43, 436/52, 53, 63, 174, 178, 180; 73/1.01, 1.02, 73/53.01

See application file for complete search history.

(56) References Cited

U.S. PATENT DOCUMENTS

| | | | | |
|---|---|---|---|---|
| 5,011,608 A | * | 4/1991 | Damjanovic ............ | 210/656 |
| 5,186,895 A | * | 2/1993 | Onofusa et al. ........ | 422/67 |
| 5,320,966 A | * | 6/1994 | Mitsumaki et al. ..... | 436/47 |
| 5,411,708 A | * | 5/1995 | Moscetta ................ | 422/81 |
| 5,726,750 A | * | 3/1998 | Ito et al. ................ | 356/244 |
| 5,789,250 A | * | 8/1998 | Ikezaki .................. | 436/20 |

FOREIGN PATENT DOCUMENTS

| | | |
|---|---|---|
| DE | 198 12 519 A1 | 9/1999 |
| EP | 0 339 440 A2 | 2/1989 |
| EP | 0 878 711 A1 | 11/1998 |
| JP | 09 091534 | 4/1997 |
| JP | 2000 076541 A | 3/2000 |

OTHER PUBLICATIONS

"Automated Charicterization of the Bitterness Unit of Wort and Beer Using a Flow Injection Analysis System", Shuso Sakuma et al., Hitachi Review, vol. 43, No. 4 (1994), p. 178, Col. 2.

"Before the Injection-Modern Methods of Sample Preparation for Separation Techniques", Roger M. Smith, Journal of Chromatography A, vol. 1000, No. 1-2, Jun. 6, 2003, pp. 3-27.

* cited by examiner

*Primary Examiner*—Jill Warden
*Assistant Examiner*—Brian Sines
(74) *Attorney, Agent, or Firm*—Rader, Fishman & Grauer PLLC (57) ABSTRACT

Taste recognition is performed by letting a solvent flow through a holding section which holds an object to be recognized and measuring the solvent which has flowed through the holding section by a taste sensor. If the flow rate of the solvent is set at about 1 ml/min, the solvent whose quantity is almost equal to that of saliva secreted in a mouth can be supplied to the object to be recognized, and hence the taste recognition can be performed by the taste sensor.

4 Claims, 6 Drawing Sheets

TASTE RECOGNITION SYSTEM AND RECOGNITION METHOD

BACKGROUND OF THE INVENTION

1. Field of the Invention

The present invention relates to a system and a method for recognizing the taste of an object to be recognized.

2. Description of the Related Art

Oral medicines such as a tablet, a troche, a powder have various tastes. The taste of such an oral medicine is recognized by a method using a so-called sensory test in which a human being called a panel member or a panelist actually takes and tastes the medicine. Moreover, recently, in order to eliminate the influence of the difference among individual panelists and their physical conditions, a lipid membrane taste sensor for performing taste recognition by measuring membrane potentials by the use of artificial lipid membranes and polymers and an ion sensitive FET (Field Effect Transistors) taste sensor appear on the market, and by using these taste sensors, the taste of the oral medicine can be recognized objectively (without a human being). Conventionally, when the taste of an oral medicine other than a liquid medicine is recognized by using such a taste sensor, the taste is measured by completely dissolving or suspending the oral medicine in 80 ml to 100 ml of water and putting the taste sensor in a solution or a suspension.

In an actual mouth, however, the oral medicine in a solid or semi-solid state is seldom dissolved completely, and a tongue tastes the oral medicine which has started to dissolve by a small quantity of saliva secreted at about 1 ml per minute. Therefore, in a conventional method of completely dissolving the oral medicine in 80 ml to 100 ml of water or anything to measure the taste by the taste sensor, the tastes of oral medicines other than the liquid medicine can not be recognized in a state close to actuality.

SUMMARY OF THE INVENTION

The present invention is made in view of such a point, and its object is to provide a mechanism capable of recognizing the taste of a solid or semisolid medicine or food taken orally, or a medicine, food or the like held in a solid or semi-solid state in a mouth in a state closest to actuality.

According to the present invention, a taste recognition system for performing taste recognition by dissolving or suspending an object to be recognized in a solvent, comprising: a holding section for holding the object to be recognized; a delivery flow path for delivering the solvent to the holding section; and a taste sensor for measuring a taste of the solvent which has flowed through the holding section is provided.

As the object to be recognized, an oral medicine such as a tablet, a troche, an oral mucous membrane plaster, a powder, an easy-to-crumble tablet, a fine particle medicine is shown as an example, but food in addition to the oral medicine, food to be masticated, lemonade candy, gummy, and so on are included in the objects to be recognized. As the solvent, a phosphate buffer and inorganic solvents including water can be used, and an organic solvent also may be used. The pH of the solvent is preferably adjusted at about 5 to about 9, and more preferably at about 6.2 to about 7.6. As the taste sensor, a lipid membrane taste sensor such as SA402 manufactured by Anritsu Corporation for performing taste recognition by measuring potentials with eight kinds of artificial lipid membranes and polymers and an ion sensitive FET (Field Effect Transistors) taste sensor such as α ASTREE manufactured by Alpha M.O.S (France, Its General Agency in Japan is Primetech Corporation) are used, but other newly developed taste sensors also may be used.

In this taste recognition system, by using a delivery pump or the like, the solvent is made to flow through the delivery flow path and supplied to the holding section which holds the object to be recognized. In this case, it is recommended to set the flow rate of the solvent, for example, at about 1 ml/min. It is said that the quantity of human saliva secretion per one day (1440 min) is about 1 liter to about 1.5 liters. Although there is a variable factor such that the quantity of saliva secretion increases when some object is taken in the mouth, if the flow rate of the solvent is set at about 1 ml/Min, the solvent whose quantity is almost equal to that of saliva secreted in the mouth can be supplied to the object to be recognized held in the holding section.

The object to be recognized and the solvent then make contact with each other in the holding section, whereby the object to be recognized is dissolved or suspended in the solvent. The taste sensor is brought into contact with the solvent in which the object to be recognized is dissolved or suspended by the solvent having flowed through the holding section, and measures the solvent to perform taste recognition.

Incidentally, it is recommended to place the holding section and the taste sensor, for example, in a constant temperature bath, and maintain them at a temperature almost equal to a human body temperature. If so, the object to be recognized is dissolved or suspended in the solvent under almost the same temperature condition as in the mouth, whereby taste recognition can be performed by the taste sensor under almost the same temperature condition as in the mouth.

Furthermore, according to the present invention, a taste recognition system for performing taste recognition by dissolving or suspending taste substances contained in an object to be recognized in a solvent, comprising: a supporting mechanism for supporting the object to be recognized and letting the taste substances pass therethrough; a pressing mechanism for pressing the object to be recognized supported by the supporting mechanism; a catch container, filled with the solvent, for catching the taste substances which have passed through the supporting mechanism; and a taste sensor for measuring a taste of the solvent filled into the catch container is provided. Also in this taste recognition system, it is preferable to place the catch container in a constant temperature bath.

DETAILED DESCRIPTION OF THE PREFERRED EMBODIMENT

Figure 1:
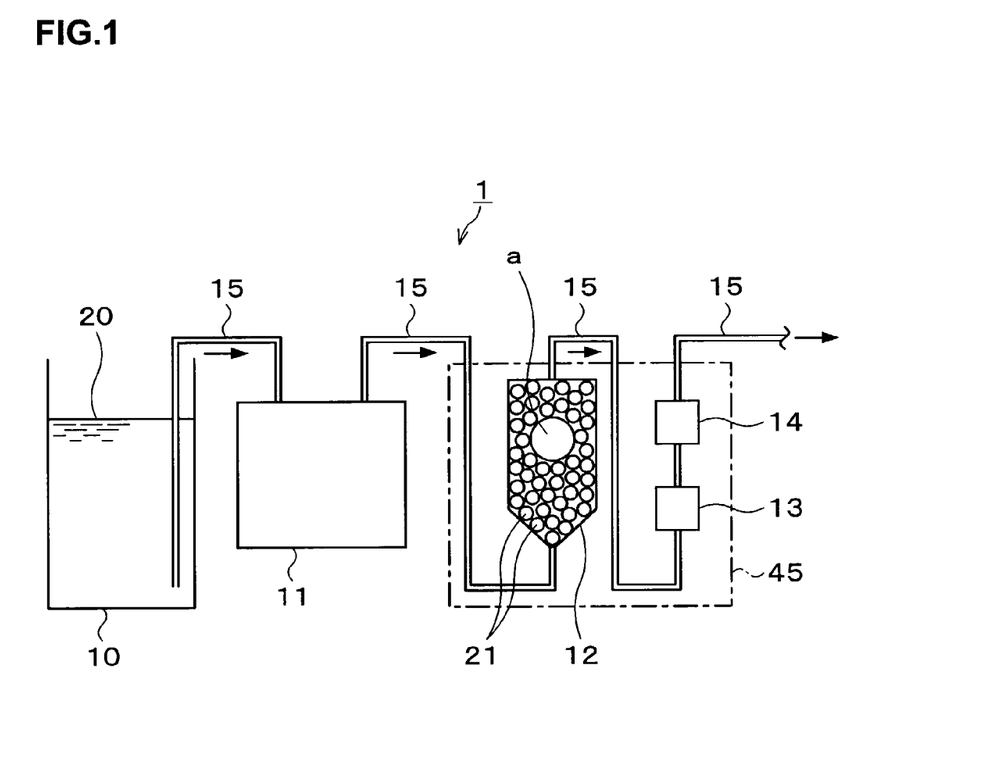
FIG. 1 is an explanatory view schematically showing the structure of a taste recognition system according to an embodiment of the present invention.

Preferred embodiments of the present invention will be described below referring to the drawings. FIG. 1 is an explanatory view schematically showing the structure of a taste recognition system 1 according to an embodiment of the present invention.

A tank 10, a delivery pump 11, a holding section 12, a first sensor section 13, and a second sensor section 14 are connected in series by a flow path 15. A solvent 20 of a phosphate buffer whose pH is adjusted at about 6.2 to about 7.6 is filled into the tank 10. The solvent 20 in the tank 10 is drawn up by the delivery pump 11 and flows through the flow path 15, so that it is delivered rightward in FIG. 1 in the order of the holding section 12, the first sensor section 13, and the second sensor section 14.

In the holding section 12, an object to be recognized (a) is held. In an illustrated example, as the object to be recognized (a), an oral medicine such as a tablet, a troche, or a powder is held in the holding section 12. The holding section 12 is filled with holding members 21 made of materials such as glass beads which are insoluble in the solvent 20. By arranging the holding members 21 around the object to be recognized (a) in the holding section 12, the object to be recognized (a) is held in such a way to be surrounded by the holding members 21 and in such a manner not to flow out from among the holding members 21 in a state in which the solvent 20 can flow therethrough.

Figure 2:
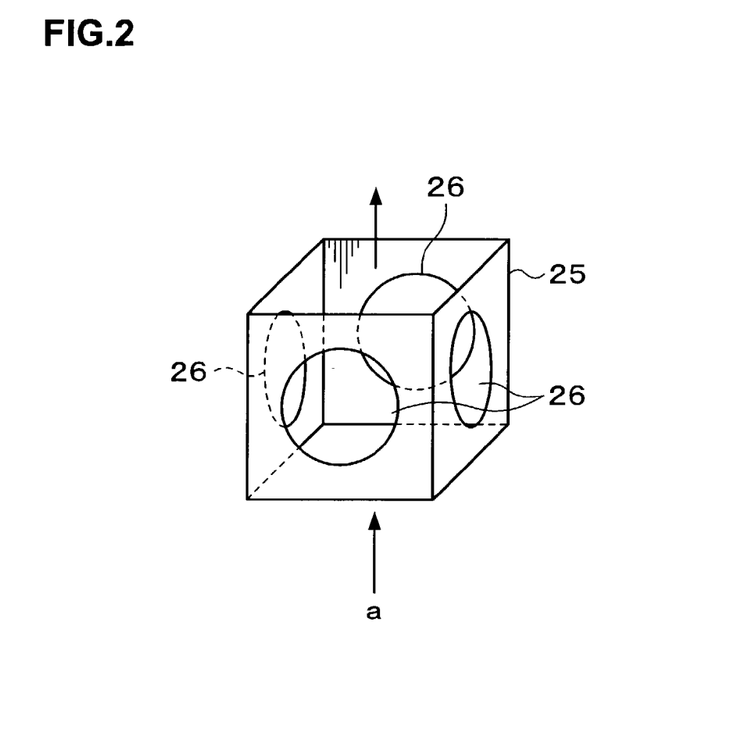
FIG. 2 is a perspective view of a measuring container.

Both of the first sensor section 13 and the second sensor section 14 have the same structure, and a measuring container 25 as shown in FIG. 2 is provided in each of these first sensor section 13 and second sensor section 14. The measuring container 25 has a prism shape with their upper and lower faces open, and in an illustrated example, the solvent 20 flows in the direction from bottom to top within the measuring container 25. The internal volume of the measuring container 25 is preferably about 1 cm$^3$. A hole 26 is formed in each of four side faces of the measuring container 25, and a taste sensor 30 described later is inserted into each of these holes 26.

Figure 3:
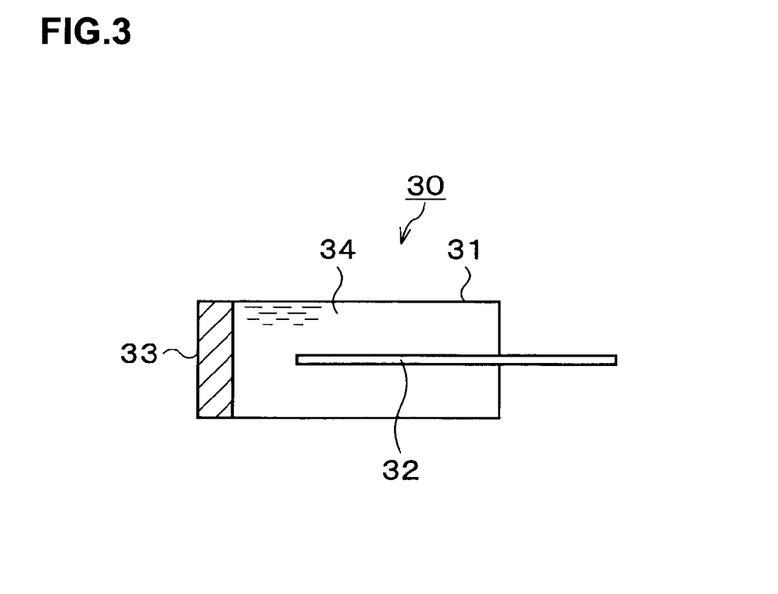
FIG. 3 is an explanatory view of a taste sensor.

As shown in FIG. 3, the taste sensor 30 has a structure in which a sensor electrode 32 is inserted into a sensor container 31, and a lipid membrane 33 is attached to a front end of the sensor container 31. The interior of the sensor container 31 is filled with an internal liquid 34 of 3M KCl+saturated AgCl water solution, and the internal liquid 34 is in contact with the periphery of the sensor electrode 32. The lipid membrane 33 is an artificial membrane formed in imitation of a living body by fixing a lipid, which performs an important function to sense a taste, with a high polymer compound.

Figure 4:
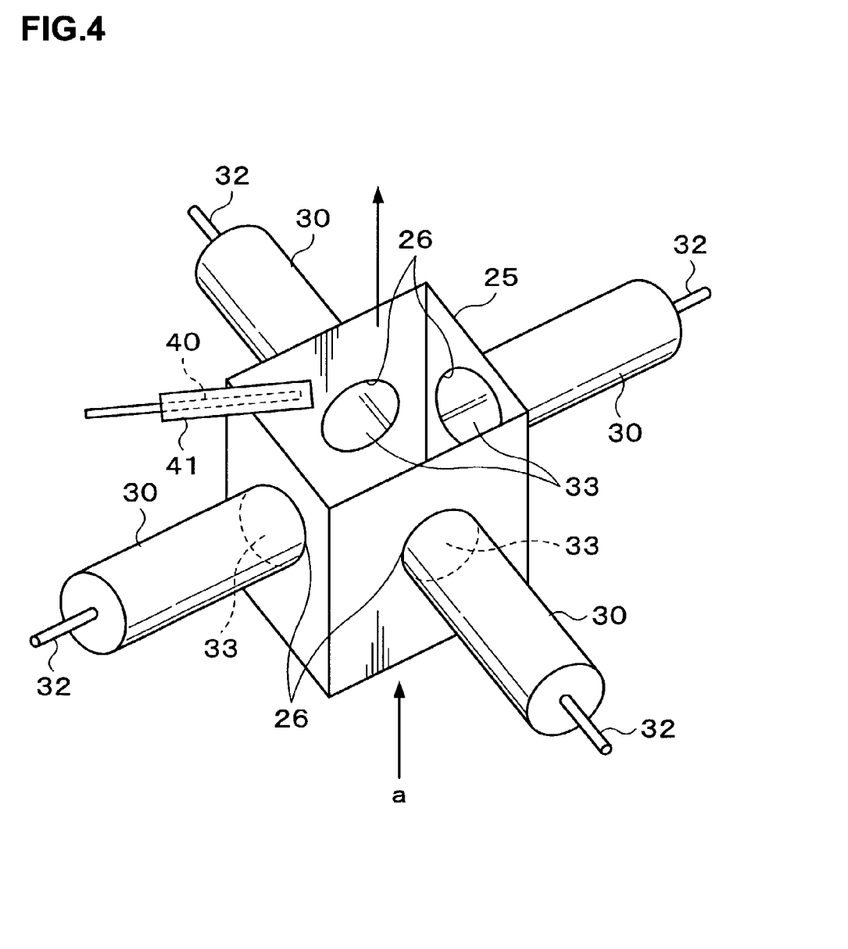
FIG. 4 is a perspective view of a state in which four taste sensors are attached to four side faces of the measuring container.

As shown in FIG. 4, by inserting a front end of the taste sensor 30 into each of the holes 26 formed in the four side faces of the measuring container 25, four taste sensors 30 are attached to one measuring container 25, and the lipid membranes 33 at the front ends of the respective taste sensors 30 are exposed to the interior of the measuring container 25. Hence, when the solvent 20 flows in the direction from bottom to top in the measuring container 25 as described above, the solvent 20 comes into contact with four lipid membranes 33 exposed to the interior of the measuring container 25.

In the illustrated embodiment, one measuring container 25 is arranged in each of the first sensor section 13 and the second sensor section 14, the solvent 20 comes into contact with the lipid membranes 33 of four taste sensors 30 in the first sensor section 13, and similarly, the solvent 20 also comes into contact with the lipid membranes 33 of four taste sensors 30 in the second sensor section 13. Thus, the solvent 20 flowing through the flow path 15 comes into contact with the lipid membranes 33 of eight taste sensors 30 in all (Incidentally, as described later, the number of taste sensors 30 is not limited to eight).

The eight sensors 30 thus arranged in the first sensor section 13 and the second sensor section 14 include the lipid membranes 33 which are made of membrane materials (lipids) different in property, respectively. Thereby, as described later, various taste substances contained in the solvent 20 come into contact with the lipid membranes 33 of the respective sensors 30 and selectively adsorbed.

Incidentally, in the illustrated example, the taste sensors 30 provided with the lipid membranes 33 each made of a negatively charged membrane material are arranged in the first sensor section 13, and the taste sensors 30 provided with the lipid membranes 33 each made of a positively charged membrane material are arranged in the second sensor section 14. Therefore, it is possible that in the first sensor section 13, positively charged taste substances (bitter ingredients) such as quinine hydrochloride are selectively adsorbed by the lipid membranes 33 of the respective taste sensors 30, and on the other hand, in the second sensor section 14, negatively charged taste substances such as iso-alpha-acid (a principal bitter substance of beer) are selectively adsorbed by the lipid membranes 33 of the respective taste sensors 30.

When the taste substance is adsorbed by the lipid membrane 33, the membrane potential of the lipid membrane 33 is changed. The membrane potential of the lipid membrane 33 thus changed by the adsorption of the taste substance is measured by the sensor electrode 32 placed in the internal liquid 34 within the sensor container 31. The membrane potential measured by the sensor electrode 32 in each of the eight taste sensors 30 is inputted to an computing mechanism not illustrated.

Moreover, as shown in FIG. 4, a reference electrode 40 is placed close to the measuring container 25, in a position to enable contact with the solvent 20 which flows upward within the measuring container 25. The periphery of the reference electrode 40 is wrapped with agar 41, and the potential of the solvent 20 flowing in the measuring container 25 is measured by the reference electrode 40 via the agar 41. The potential of the solvent 20 measured by the reference electrode 40 is inputted to the computing mechanism not illustrated.

The computing mechanism not illustrated measures changes in membrane potential measured by the sensor electrodes 32 in the respective eight taste sensors 30 with the potential of the solvent 20 measured by the reference electrode 40 as a reference, performs computing processing of values measured by the respective taste sensors 30, and recognizes taste by pattern recognition or the peculiarities of the respective lipid membranes 33 for various kinds of tastes. Incidentally, the method of recognizing taste by performing computing processing of plural signals obtained from the respective taste sensors 30 by the use of the respective sensors 30 provided with eight different kinds of lipid membranes 33 can be implemented by a technique disclosed in Japan Society of Pharmaceutical Machinery and Engineering Journal Vol. 6, No. 4 (1997) (Akira Taniguchi, Chief researcher of Sensing Technology Project Team, Research Laboratory, Anritsu Corporation).

As shown in FIG. 1, all of the holding section 12, the first sensor section 13, and the second sensor section 14 are placed in a constant temperature bath 45. The constant temperature bath 45 is filled with a heat medium such as warm water, whereby all of the holding section 12, the first sensor section 13, and the second sensor section 14 are maintained at a temperature almost equal to a human body temperature.

In the taste recognition system 1 according to the embodiment of the present invention structured as above, by the operation of the delivery pump 11, the solvent 20 in the tank 10 is delivered in the order of the holding section 12, the first sensor section 13, and the second sensor section 14 via the flow path 15. In this case, it is recommended to set the flow rate of the solvent 20, for example, at about 1 ml/min. In so doing, the solvent 20 whose quantity is almost equal to that of saliva secreted per unit time in a human mouth can be delivered.

The solvent 20 thus delivered via the flow path 15 first flows through the holding section 12, and on this occasion, makes contact with the object to be recognized (a). Thereby, the object to be recognized (a) is dissolved or suspended in the solvent 20, and turns into taste substances, which flow out together with the solvent 20. The solvent 20 (the solvent 20 containing the taste substances) in which the object to be recognized (a) is dissolved or suspended by having flowed through the holding section 12 as described above is further delivered via the flow path 15, and then flows through the first sensor section 13 and the second sensor section 14.

Thus, the solvent 20 flows through the interior of the measuring container 25 in the direction from bottom to top in each of the first sensor section 13 and the second sensor section 14, and on this occasion comes into contact with each of the eight lipid membranes 33 exposed to the interiors of the measuring containers 25. Consequently, various kinds of taste substances contained in the solvent 20 are selectively adsorbed by the lipid membranes 33 of the respective taste sensors 30.

When the taste substances are adsorbed by the lipid membranes 33, the membrane potentials of the lipid membranes 33 change, and these membrane potential changes are measured by the sensor electrodes 32 of the respective taste sensors 30 and inputted to the computing mechanism not illustrated. The computing mechanism performs computing processing of the membrane potential changes measured by the sensor electrodes 32 in the respective eight taste sensors 30 with reference to the potential of the solvent 20 measured by the reference electrode 40, and performs taste recognition by statistical analysis such as multivariate analysis (main ingredient analysis or discriminant analysis).

According to this taste recognition system 1, by delivering the solvent 20 at 1 ml/min by the delivery pump 11, the object to be recognized (a) can be dissolved or suspended in the solvent 20 under almost the same condition as in the human mouth in the holding section 12 placed within the constant temperature bath 45. Moreover, by delivering the solvent 20, in which the object to be recognized (a) is dissolved or suspended under the same condition as in an actual mouth, to the first sensor section 13 and the second sensor section 14 and measuring it by the taste sensors 30, taste recognition can be performed in the constant temperature bath 45 under almost the same condition as in the mouth.

In the above description, an example of the preferred embodiment of the present invention is explained, but the present invention is not limited to the embodiment illustrated above. For example, in addition to a lipid membrane taste sensor such as SA402 manufactured by Anritsu Corporation, an ion sensitive FET (Field Effect Transistors) taste sensor such as α ASTREE manufactured by Alpha M.O.S (France, Its General Agency in Japan is Primetech Corporation) can be used as the taste sensor 30. Moreover, in addition to the phosphate buffer, inorganic solvents including water, and organic solvents may be used as the solvent 20. Furthermore, as the object to be recognized (a), food and others besides the oral medicine may be used.

In the illustrated embodiment, the example, in which the four taste sensors 30 are arranged in the measuring container 25 provided in each of the first sensor section 13 and the second sensor section 14, and hence the eight taste sensors 30 in all are arranged, is explained, but the number of the taste sensors 30 is arbitrary, and, for example, the number of the taste sensors 30 may be reduced to seven or less by closing part of the holes 26 with blind patches or the like. Further, it is suitable to provide one taste sensor 30 in the measuring container 25. Furthermore, the shape of the measuring container 25 provided in each of the first sensor section 13 and the second sensor section 14 need not be a prism shape.

Incidentally, the percentage of voids in the holding section 12 can be set as desired by adjusting the quantity of the holding members 21 filled into the holding section 12, and the same condition as in the actual mouth can be reproduced. Moreover, it is recommended that as in this embodiment, the taste sensors 30 each provided with the lipid membrane 33 made of the negatively charged membrane material be arranged in the first sensor section 13 on the upstream side of the flow path 15, and the taste sensors 30 each provided with the lipid membrane 33 made of the positively charged membrane material be arranged in the second sensor section 13 on the downstream side of the flow path 15. In so doing, there is no possibility that lipid dissolved in the solvent 20 from the lipid membranes 33 each made of the positively charged membrane material in the second sensor section 14 adheres to the lipid membranes 33 (lipid membranes 33 each made of the negatively charged membrane material) in the first sensor section 13. Incidentally, when the ion sensitive taste sensor is used, such consideration is unnecessary. Moreover, when the ion sensitive taste sensor is used, it is unnecessary to separate the first sensor section 13 and the second sensor section 14.

Figure 5:
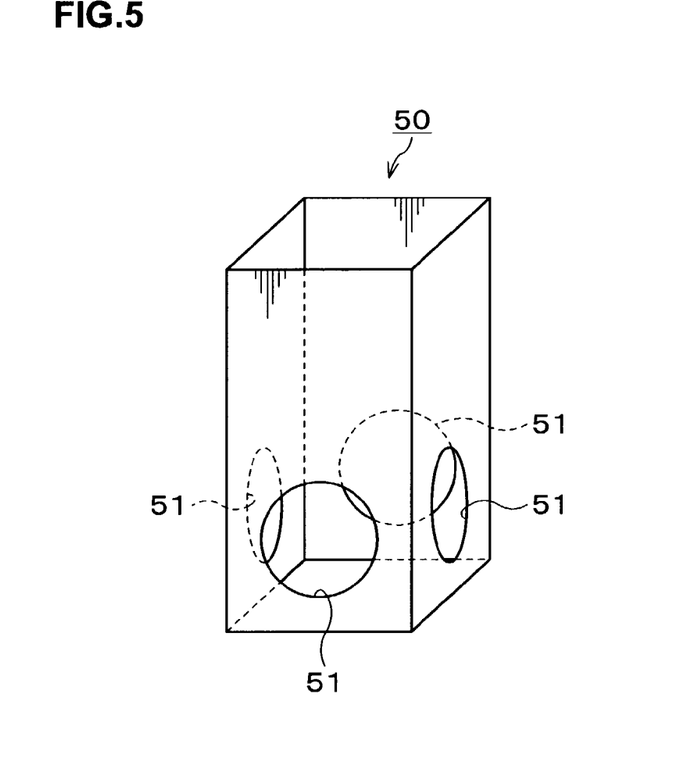
FIG. 5 is a perspective view of a measuring container as another example.

Furthermore, in the illustrated embodiment, the example, in which the first sensor section 13 and the second sensor section 14 are provided midway in the flow path 15, but it is possible to perform taste measurement in batch mode by using a measuring container 50 as shown in FIG. 5. The measuring container 50 shown in FIG. 5 has a prism shape with its upper face open and its lower face closed, and the solvent 20 can be stored in the measuring container 50 by pouring the solvent 20 from above the measuring container 50. Holes 51 are formed in four side faces of this measuring container 50, respectively, the front ends of the taste sensors 30 described previously are inserted into the holes 51, respectively, and thus the lipid membranes 33 at the front ends of the respective taste sensors 30 can be exposed to the interior of the measuring container 50. It is also possible to pour the solvent 20 into such a measuring container 50, put the object (a) therein, and measure the taste in batch mode. By measuring potentials continuously, taste changes with time come to be shown. In this case, it is recommended that the quantity of the solvent 20 poured into the measuring container 50 be 1 ml, but, of course, the quantity is not limited to this quantity.

Figure 6:
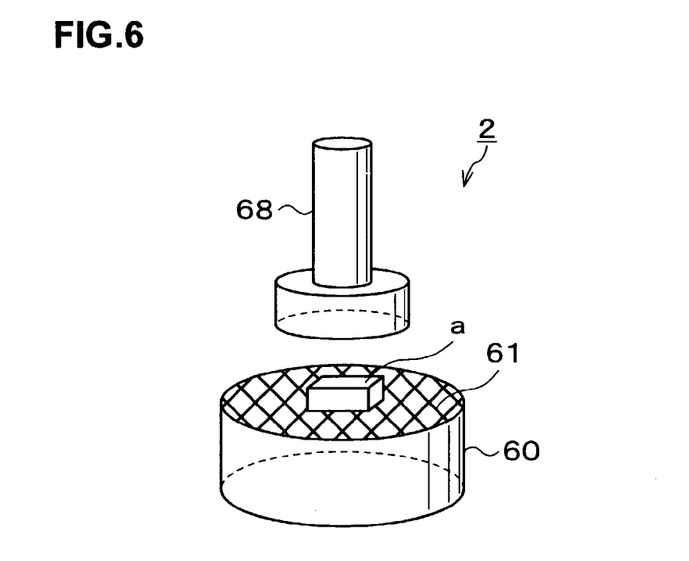
FIG. 6 is a perspective view schematically showing the structure of a taste recognition system according to another embodiment of the present invention.

Next, FIG. 6 is a perspective view schematically showing the structure of a taste recognition system 2 according to another embodiment of the present invention. In this taste recognition system 2, a mesh 61 as a supporting mechanism is attached to an opening of an upper face of a catch container 60. The interior of the catch container 60 is filled with a solvent of a phosphate buffer whose pH is adjusted at about 6.2 to about 7.6. A stirrer bar 65 for stirring the solvent is placed at the center of a bottom face of the catch container 60, and four lipid membranes 66 constituting taste sensors and a reference electrode 67 are arranged around the stirrer bar 65.

In the taste recognition system 2 thus structured, the object to be recognized (a) is placed on the mesh 61 and pressed from above by a plunger 68 as a pressing mechanism. The taste substances contained in the object to be recognized (a) are made to flow down through the mesh 61, and dissolved or suspended in the solvent within the catch container 60. Consequently, the taste substances are adsorbed by the lipid membranes 66, and taste recognition becomes possible in the same manner as above.

According to this taste recognition system 2, by being pressed by the plunger 68, the object to be recognized (a) can be measured under the same condition as in the case where the object to be recognized (a) is masticated. It is preferable that the pressing force of the plunger 68 can be changed optionally corresponding to the object to be recognized (a). Moreover, by measuring the pressing force of the plunger 68 necessary to press the object to be recognized (a), the texture necessary for mastication can be known, whereby new taste data (texture data) can be obtained.

Incidentally, in the same manner as stated previously, the catch container 60 may be placed in a constant temperature bath or a band heater (not illustrated). In so doing, taste recognition can be performed under almost the same condition in the human mouth. Moreover, it is appropriate that each aperture of the mesh 61 is about 1 mm to about 5 mm, and the provision of sufficient strength is recommended.

Figures 7, 8:
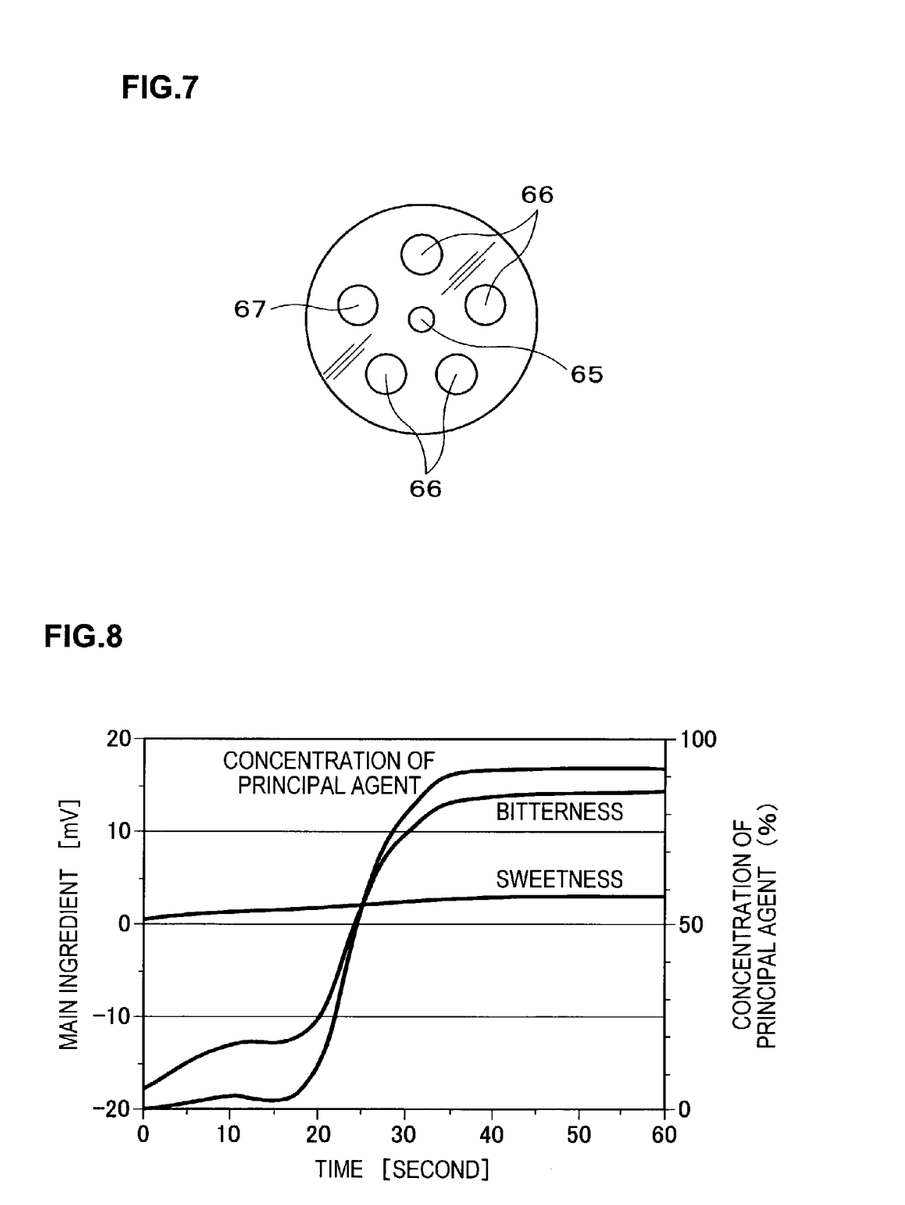
FIG. 7 is a bottom view of a catch container in a measuring container according to the aforementioned another embodiment.
FIG. 8 is a graph showing an experiment of the present invention.

Taste measurement is performed by using the taste recognition system shown in FIG. 1. First, one gram of fine particle medicine as the object to be recognized is held in the holding section, the solvent is delivered at a flow rate of 1 ml/min, and then measured in the first and second sensor sections. Consequently, results shown in FIG. 8 are obtained. The concentration of a principal agent is defined as 100% when all of one gram of particle medicine is dissolved. Since 92% of the principal agent is dissolved in one minute, it is expected that in the case of the entire particle medicine, almost the same percentage of particle medicine is dissolved. Regarding ingredient mixture, a sweetening agent is considerably more than the principal agent which tastes bitter, and hence if their concentrations are simply compared, sweetness ought to increase with a lapse of time. However, in actuality, a human being can recognize bitterness more sharply than sweetness. As expected, it is shown that the taste recognition system shown in FIG. 1 also reacts more sharply to bitterness than to sweetness, and taste close to that recognized in the mouth by means of human sensibilities can be measured with a lapse of time.

Figure 9:
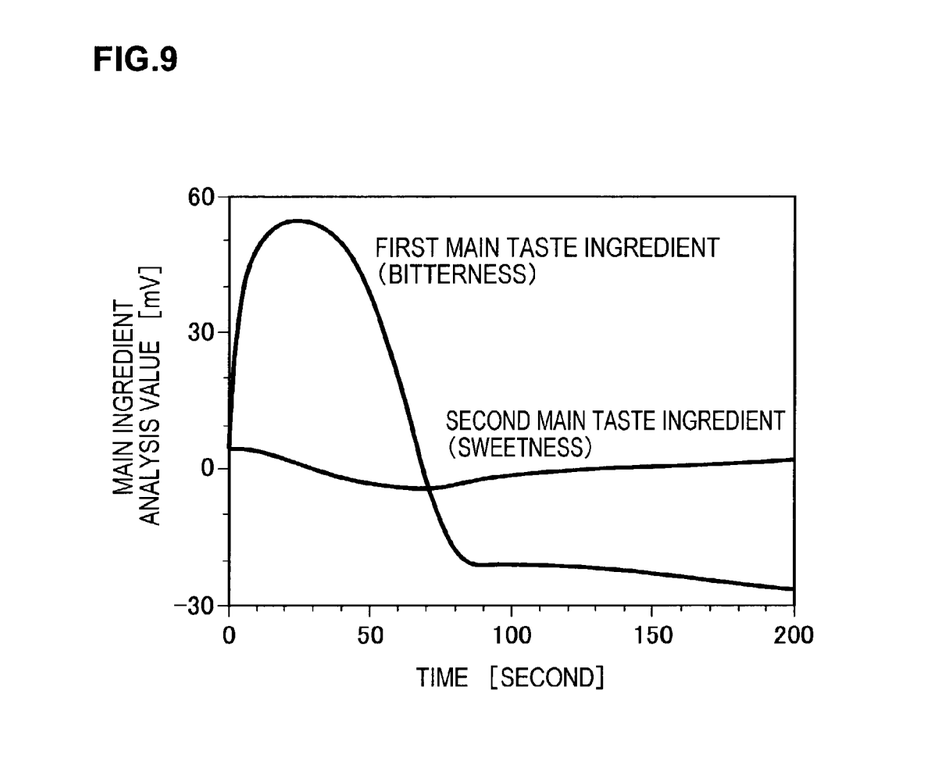
FIG. 9 is a graph showing an experiment of the present invention.

Next, in the taste recognition system shown in FIG. 1, an oral mucous membrane plaster (brand name: "Nitrofix") containing isosorbide nitrate as an active ingredient, as the object to be recognized, is held in the holding section and measured. Consequently, results shown in FIG. 9 are obtained. It is found that the taste of a first taste ingredient (bitter ingredient) becomes gradually stronger and then becomes gradually weaker as time passes. A second taste ingredient (sweet ingredient) hardly changes. The object to be recognized which has very little taste is measured in this example, but this system is also useful for an oral mucous membrane plaster, a troche, or the like which has a strong taste.

According to the present invention, it becomes possible to recognize the taste of the object to be recognized with a lapse of time in a state closest to actuality. According to the present invention, the taste of the object to be recognized can be measured in a solid state, and hence it is unnecessary to dissolve objects to be recognized one by one in the solvent.

What is claimed is:

1. A taste recognition system for performing taste recognition by dissolving or suspending taste substances contained in an object to be recognized in a solvent, comprising:
   a supporting mechanism for supporting the object to be recognized and letting the taste substances pass therethrough;
   a pressing mechanism for pressing the object to be recognized supported by said supporting mechanism;
   a catch container, filled with the solvent, for catching the taste substances which have passed through said supporting mechanism; and
   a taste sensor for measuring a taste of the solvent filled into said catch container.

2. A taste recognition system as set forth in claim 1, wherein said catch container is placed in a constant temperature bath.

3. A method for performing taste recognition comprising:
   delivering a solvent to a holding section which holds an object to be recognized,
   dissolving or suspending the object to be recognized in the solvent,
   measuring via a taste sensor the solvent which has flowed through the holding section,
   wherein said holding section comprises a holding member which prevents said object from flowing out from said holding member and allows the solvent to flow through said object.

4. A method for performing taste recognition as set forth in claim 3, wherein said solvent is delivered at a flow rate of about 1 ml/min.

* * * * *